United States Patent
Kranz

[11] Patent Number: 6,102,956
[45] Date of Patent: Aug. 15, 2000

[54] MODULAR ENDOPROSTHESIS

[75] Inventor: Curt Kranz, Berlin, Germany

[73] Assignee: ARTOS Medizinische Produkte GmbH, Berlin, Germany

[21] Appl. No.: 09/068,955

[22] PCT Filed: Sep. 4, 1996

[86] PCT No.: PCT/DE96/01713

§ 371 Date: May 20, 1998

§ 102(e) Date: May 20, 1998

[87] PCT Pub. No.: WO97/18776

PCT Pub. Date: May 29, 1997

[30] Foreign Application Priority Data

Nov. 20, 1995 [DE] Germany ............... 195 44 168

[51] Int. Cl.[7] ......................................... A61F 2/32
[52] U.S. Cl. ................................................ 623/22
[58] Field of Search ................... 623/18, 19, 22, 623/23

[56] References Cited

U.S. PATENT DOCUMENTS

| 3,846,846 | 11/1974 | Fischer | 623/23 |
|---|---|---|---|
| 4,676,797 | 6/1987 | Anapliotis et al. | 623/18 |
| 4,808,186 | 2/1989 | Smith . | |
| 4,878,917 | 11/1989 | Kranz et al. | 623/18 |
| 5,074,879 | 12/1991 | Pappas et al. | 623/18 |
| 5,645,600 | 7/1997 | Bimman | 623/18 |
| 5,653,764 | 8/1997 | Murphy | 623/18 |

FOREIGN PATENT DOCUMENTS

| 0332571 | 9/1989 | European Pat. Off. . | |
| 0457222 | 11/1991 | European Pat. Off. . | |
| 0550117 | 7/1993 | European Pat. Off. . | |
| 0611558 | 8/1994 | European Pat. Off. . | |
| 0190981 | 8/1996 | European Pat. Off. | 623/18 |
| 2606628 | 5/1988 | France . | |
| 3340767 | 5/1985 | Germany . | |
| 3802213 | 7/1989 | Germany . | |
| 8903850 U | 7/1989 | Germany . | |
| 4031520 | 4/1992 | Germany . | |
| 9418963 | 1/1995 | Germany | 623/18 |
| 295 06 036 U | 7/1995 | Germany . | |
| 001667854 | 8/1991 | U.S.S.R. | 623/18 |
| 9118559 | 12/1991 | WIPO | 623/18 |
| 96/15739 | 5/1996 | WIPO . | |

Primary Examiner—Jeffrey A. Smith
Assistant Examiner—Eduardo C. Robert
Attorney, Agent, or Firm—Venable; George H. Spencer; Robert Kinberg

[57] ABSTRACT

A modular endoprosthesis having a plurality of shaft elements, wherein a first shaft element has a longitudinal axis, an outer wall, a circumferential indentation and a substantially conical bore. The bore has an open mouth and a closed base. The circumferential indentation is located on the outer wall close to the open mouth of the conical bore for the purpose of reducing mechanical stresses in the vicinity of the mouth of the bore when the endoprosthesis is subjected to a bending force. A second shaft element has a longitudinal axis, an outer wall and a substantially conical pin adapted to fit the bore in the first shaft element, for joining the two shaft elements together with a conical socket connection.

10 Claims, 3 Drawing Sheets

MODULAR ENDOPROSTHESIS

BACKGROUND OF THE INVENTION

The invention relates to a modular endoprosthesis, particularly a femur prosthesis, which has a conical socket connection, with a first shaft element having a substantially conical bore, a second shaft element having a substantially conical pin adapted to fit the bore in the first shaft element, for connecting the two shaft elements together, wherein the first shaft element containing the bore has a circumferential indentation on its outer wall, close to the mouth end, for the purpose of reducing the mechanical load occurring on the edge of the mouth of the bore under bending stress.

DE 33 40 767 A1 discloses a prosthesis of this kind which consists of at least two shaft portions connected by fitting together. The mechanical connection between two shaft elements is achieved here by pressing a conical pin formed on one shaft element into a conical bore provided in the other shaft element so as to obtain a press fit.

As the endoprosthesis is made up of different shaft elements, endoprostheses of different shaft lengths can advantageously be produced in this way.

Moreover, the endoprosthesis can easily be removed, for example in the case of a repeat operation, by separating the shaft elements from one another and removing them one by one.

A disadvantage of the known endoprosthesis is, however, that the shaft element which contains the conical socket may have pronounced wear caused by microscopic movements in the region of the rim of the mouth, which may lead to cracking in extreme cases.

SUMMARY OF THE INVENTION

The aim of the invention is therefore to prevent these manifestations of wear in a modular endoprosthesis of this kind.

The aim is achieved by means of a modular endoprosthesis, comprising: a first shaft element having a first end, a second end, a longitudinal axis, an outer wall, a circumferential indentation and a substantially conical bore, wherein the bore includes an open mouth and a closed base; and a second shaft element having a first end, a second end, a longitudinal axis, an outer wall and a substantially conical pin adapted to fit the bore in the first shaft element, for joining the two shaft elements together with a conical socket connection. The circumferential indentation of the first shaft element is located on the outer wall close to the open mouth of the conical bore for the purpose of reducing mechanical stresses in the vicinity of the mouth of the bore when the endoprosthesis is subjected to a bending force.

The invention includes the technical teaching of shaping the shaft element of an endoprosthesis of this kind with a conical bore so as to avoid local peaks in mechanical stress in the region of the rim of the mouth of the bore.

The invention starts from the finding that the known shaft element containing the conical socket was too rigid in construction in the rim area, so that, in the event of bending stresses on the endoprosthesis with a corresponding offsetting of the longitudinal axes of the pin and bore, there was a reduction in the effective frictional forces between the pin and the bore, resulting in local microscopic movements.

Thus, the stress-absorbing contact area when the endoprosthesis is subjected to bending stress corresponds substantially to the entire surface area of the conical pin. As the bending stress increases and the longitudinal axes of the pin and bore are offset more and more as a result, the transmissible frictional forces are reduced. This leads to local movements at the rim of the mouth of the bore, which may lead to abrasion and cracking.

Since the bending stress acting on the endoprosthesis is not constant over time but is subject to fluctuations in its degree and direction depending on the natural loading conditions of the endoprosthesis, oscillating microscopic movements occur between the pin and bore. These microscopic movements together with the local stress peaks occurring at the rim of the mouth of the bore lead to the abrasion of material and hence to premature wear, which is also known as fretting.

According to the invention, therefore, the elasticity of the shaft element is increased just before the end of the mouth of the conical bore, so that, in the event of bending stress on the endoprosthesis and accordingly offsetting of the longitudinal axes of the pin and bore, the inner wall of the bore adapts to the position of the pin and together with the outer surface of the pin forms a sufficiently large contact surface to absorb the peripheral stresses. The very end of the cone, however, retains its wall thickness in order to ensure that it still has sufficient strength in the circumferential direction. This ensures that the introduction of force in the end part of the cone is distributed over a greater length and in this way overstressing in the immediate vicinity of the mouth is avoided.

According to the invention, the shaft element having the conical bore thus comprises, on the outer wall, in the region of the bore, close to the mouth end, an indentation which runs circumferentially relative to the longitudinal axis of the bore.

This indentation or the related reduction in the wall thickness of the shaft element in the region of the bore leads to an increase in the elasticity of the shaft element, so that the inner wall of the bore fits the pin when the pin is offset relative to the bore.

The construction of the shaft element with an indentation extending around the entire circumference is advantageous as the wear-reducing effect according to the invention is then unaffected by the direction of the bending stress.

In an advantageous development of the invention, the indentation runs smoothly with large enough radii of curvature, avoiding any sharp angles. This further reduces the mechanical stress in the indentation in the outer wall of the shaft element and helps to prevent cracking.

The indentation is preferably formed so that, when the shaft element is under bending stress, the maximum mechanical stress occurring in the region of the bore is evened out as far as possible. To determine the optimum shape of the indentation, the mechanical stress occurring in the shaft element under bending stress may be calculated, for example, by numerical simulation methods for various shapes of indentations, and the shape having the lowest maximum stress is then selected from them.

In an advantageous embodiment of the invention, the indentation increases in depth along the axis of symmetry towards the end of the shaft element. This accordingly means that the wall thickness of the shaft element decreases in the region of the bore towards its end, whereas the flexibility of the pin socket increases towards the end of the shaft element. This is beneficial, because the pin socket is consequently very flexible when the pin is only slightly offset relative to the bore, thus leading to a reduction in the local stress peaks, but on the other hand becomes harder as the pin is offset more and more relative to the bore and thus ensures that the pin is reliably guided even under considerable bending stresses.

In order to achieve good biocompatibility of the endoprosthesis it is desirable for the parts which are to be implanted to have a smooth surface with no protruding edges or corners. The indentation in the shaft elements therefore preferably merges smoothly into the outer wall, without forming a kink or even a step at the point of transition.

The mechanical connection between two shaft elements is preferably obtained by frictional locking, with the pin in one shaft element and the bore in the other shaft element forming a press fit.

However, it may be desirable to connect the shaft elements in a manner which confers greater mechanical strength.

According to another alternative embodiment of the invention the shaft elements therefore have a preferably centrally positioned longitudinal channel for receiving a tie rod which makes it possible to brace the individual shaft elements against one another.

If the longitudinal channel is positioned centrally, the bending limit of the endoprosthesis is only slightly reduced by the longitudinal channel, since the stress peaks, under bending stress, occur near the edges of the shaft elements.

In a preferred embodiment of the invention, the endoprosthesis therefore comprises a plurality of shaft elements which can be fitted together to form an endoprosthesis, so that the length of the endoprosthesis can be varied by a whole-number multiple of the length of a shaft element.

However, it is often desirable to be able to graduate the length of the endoprosthesis more finely. In an advantageous alternative embodiment of the invention, the endoprosthesis therefore comprises a plurality of shaft elements of different lengths. This makes it possible, on the one hand, to put together an endoprosthesis of a specified length from very few shaft elements and, on the other hand, to achieve a very finely graduated endoprosthesis length.

BRIEF DESCRIPTION OF THE DRAWING

Other advantageous features of the invention are recited in the subordinate claims or described hereinafter together with a description of the preferred embodiment of the invention with reference to the drawings, wherein:

FIG. 2a shows the pattern of the mechanical stresses occurring in the shaft element.

DESCRIPTION OF THE PREFERRED EMBODIMENT

Figure 1:
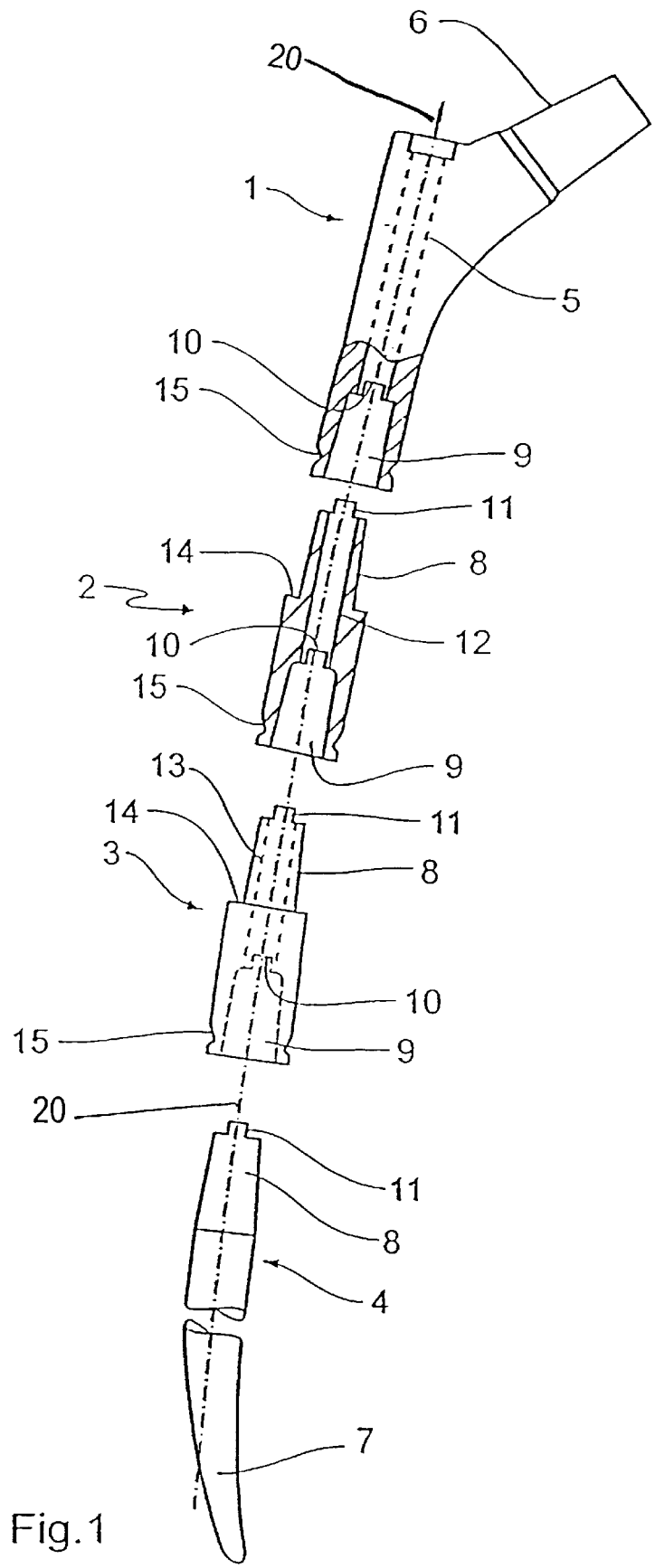
FIG. 1 shows, as a preferred embodiment of the invention, an endoprosthesis with a plurality of shaft elements in cross section.

The endoprosthesis shown in FIG. 1 is inserted in the femur.

The endoprosthesis consists essentially of four shaft elements 1, 2, 3, 4 of substantially circular cross section which are fitted into one another and, in the assembled state, form a solid unit.

The shaft element 1—hereinafter referred to as the head portion—has a pin 6 on its upper side for receiving a ball which allows it to be mounted in the socket of the pelvis.

In order to achieve optimum function of the endoprosthesis the head portion 1 is curved in its upper region in the manner of a natural femur.

Another shaft element 4—hereinafter referred to as the end portion—is used to anchor the endoprosthesis in the remaining natural bone. On the underside of the end portion 4, therefore, is formed a bone pin 7 which tapers towards its end and is intended to be cemented into the medullary space of the remaining natural bone.

For connection to one another the shaft elements 2, 3 each have a conical pin 8 formed on the top and a conical bore 9 provided on the bottom which fits the pin 8 and forms a press-fit connection therewith. Thus, when the endoprosthesis is assembled, the pin 8 of one shaft element is pressed into the bore 9 of another shaft element.

The end portion 4 merely has a pin 8 formed on the top which is pressed into the bore 9 in the shaft element 3. Accordingly, the head portion 1 only has a bore 9 provided on the underside for accommodating the pin 8 of the upper shaft element 2.

The individual shaft elements 2, 3, 4 are slightly curved, like the head portion 1, to correspond to the natural shape of a femur. To ensure that the endoprosthesis corresponds to the natural shape of a femur, the individual shaft elements 1, 2, 3, 4 must therefore be fitted into one another in the correct order, on the one hand, and in the correct angular position, on the other hand.

In order to guarantee the correct angular position when assembling the endoprosthesis and prevent rotation of the individual shaft elements 1, 2, 3, 4 in the implanted state, a groove 10 is formed on the base of the conical bore 9, into which a spring 11 formed on the pin 8 engages when two shaft elements are fitted together, thereby preventing rotation.

Occasionally, it is necessary to remove an endoprosthesis implanted earlier, for example because the prosthesis has come to the end of its useful life as a result of wear or because the patient has grown and now needs a larger endoprosthesis. In such a case, it is desirable to be able to remove the shaft elements 1, 2, 3, 4 individually, making the operation of removing the endoprosthesis considerably easier.

In order to do this, the shaft elements 1, 2, 3, 4 have to be separated from one another, which normally takes considerable force owing to the press-fit of the pins 8 and bores 9. The shaft elements 1, 2, 3 therefore each have a threaded bore 5, 12, 13 extending along the longitudinal axis 20. To separate the shaft elements, a screw is then screwed into the threaded bore from above until the screw forces the pin 8 out of the bore 9.

In the implanted state, the longitudinal forces occurring as a result of the mechanical loading of the endoprosthesis are absorbed by the abutting surfaces 14 of the shaft elements 2, 3 and by the outer surfaces of the conical pins 8 or bores 9. Additionally, however, a bending load also acts on the endoprosthesis or on the individual shaft elements 1, 2, 3, 4, leading to more wear particularly at the contact surfaces of the pin 8 and bore 9. This stems from the fact that, when the endoprosthesis is subjected to bending stress, the pin 8 which is normally aligned with the bore is offset relative to the bore 9, leading to a reduction in the effective stress-absorbing contact area between the pin 8 and bore 9 and hence to local stress peaks, particularly around the mouth of the bore 9.

The shaft elements 1, 2, 3 therefore have on their outer wall, level with the bore 9, an indentation 15 which is circumferential relative to the longitudinal axis and which increases the elasticity of the pin mounting. This means that the shaft elements 1, 2, 3 yield slightly to the pin 8 under bending stress acting on the endoprosthesis at the mouth of the bore 9, leading to an increase in the effective stress-absorbing contact area and hence to a reduction in the maximum mechanical stress occurring.

Figure 2:
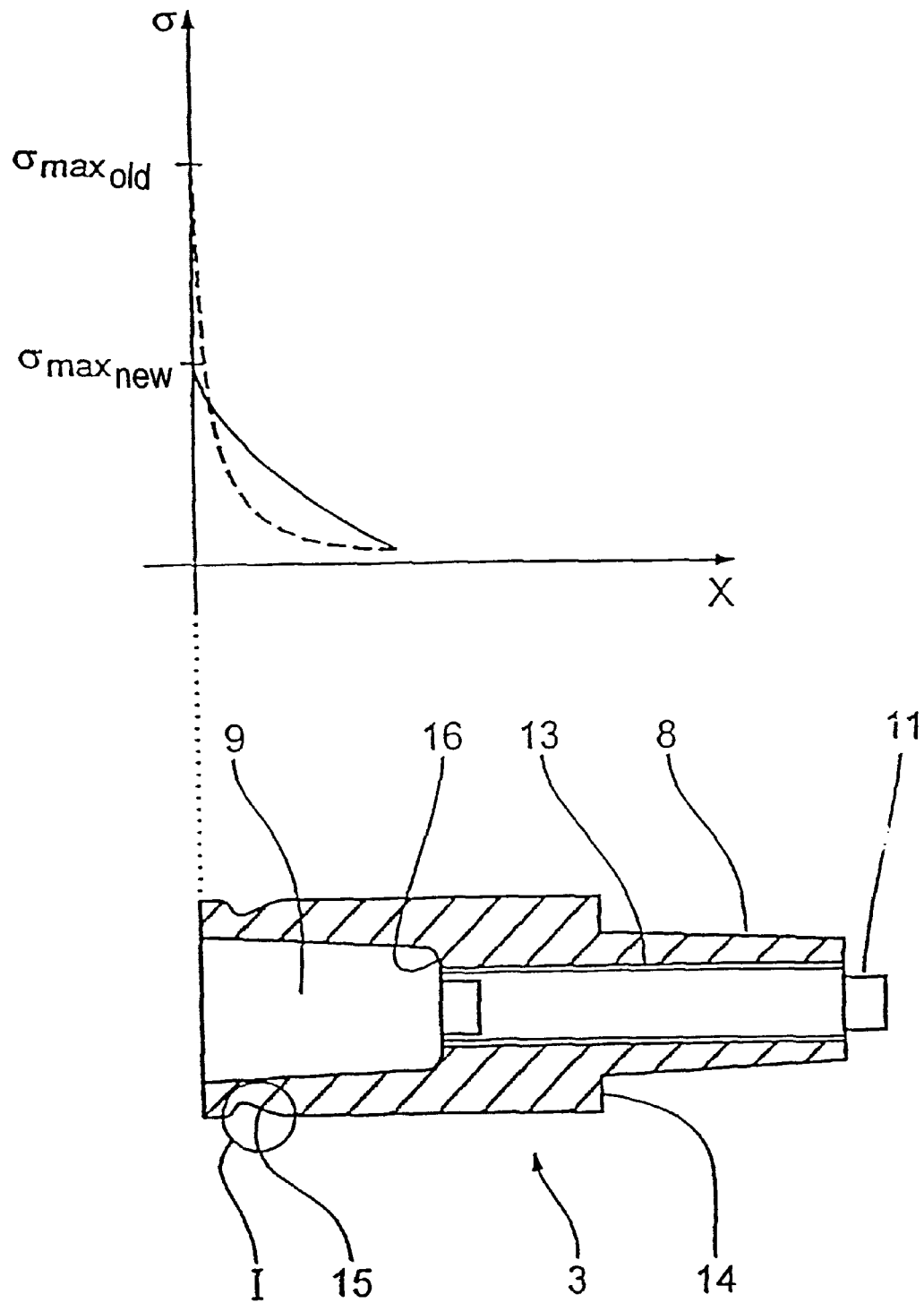
FIG. 2 shows a shaft element of the endoprosthesis shown in FIG. 1, in a detailed cross sectional view.

FIG. 2 shows, in its lower part, the shaft element 3 of the endoprosthesis shown in FIG. 1, on a larger scale, with the indentation 15 provided in the outer wall.

It is plain to see that a radius 16 is formed on the base of the conical bore 9 for reducing the mechanical stresses at the transition from the outer surface of the conical bore 9 to the bottom of the bore 9.

As a result of the weakening of the wall caused by the indentation, the force is not introduced first as a maximum peak at the end of the mouth, but instead is introduced beforehand, already evened out, from the end of the mouth in the region of the indentation. The reduction in stresses prevents overloading of the material.

The shape of the indentation 15 shown represents an ideal compromise between the need for a very rigid mounting of the pin, in order to ensure that the pin is guided reliably and substantially without play, on the one hand, and the need for sufficient flexibility of accommodation of the pin, on the other hand, in order to break down local stress peaks at the rim of the mouth of the bore 9, and to distribute the forces as uniformly as possible over a larger stress-absorbing contact area.

The indentation 15 increases in depth along the longitudinal axis of the bore 9 towards the end of the shaft element 3. Accordingly, the wall thickness of the shaft element 3 decreases in the region of the bore 9 towards the end of the shaft element 3. This results in an increasing flexibility towards the end of the shaft element 3.

Under bending stresses, the pin socket is therefore relatively yielding and adapts well to the altered position of the pin. This leads to an increase in the effective stress-absorbing contact area between the pin and bore 9 and hence in an attenuation of local stress peaks at the rim of the mouth of the bore 9.

Furthermore, FIG. 2a shows, in an associated diagram, the pattern of the mechanical stress occurring in the pin socket along the longitudinal axis of the bore (based on the view FIG. 2a). The dotted line shows, by way of a comparison, the stress pattern in an endoprosthesis known from the prior art, whereas the continuous line shows the pattern of mechanical stress in the endoprosthesis according to the invention described hereinbefore.

In the known endoprosthesis the mechanical stress increases very considerably along the longitudinal axis of the bore. Thus, the stress is relatively low in the upper part of the bore and increases to a value $\delta_{MAX,old}$ in the vicinity of the edge of the mouth, which may lead to an overload.

In the endoprosthesis according to the invention, by contrast, the stress pattern along the longitudinal axis of the bore is substantially more uniform, advantageously resulting in a substantially lower maximum stress $\delta_{MAX,new}$. This is achieved by the fact that, owing to the reduction in strength of the conical sleeve caused by the indentation, this sleeve is resiliently deformed under load at this point, so that force can be transmitted preferentially in the region of the indentation. However, the corresponding forces occur at the end of the cone. But since the original—unreduced—wall thickness is still present here, this region is stable enough to absorb the reduced forces.

Figure 3:
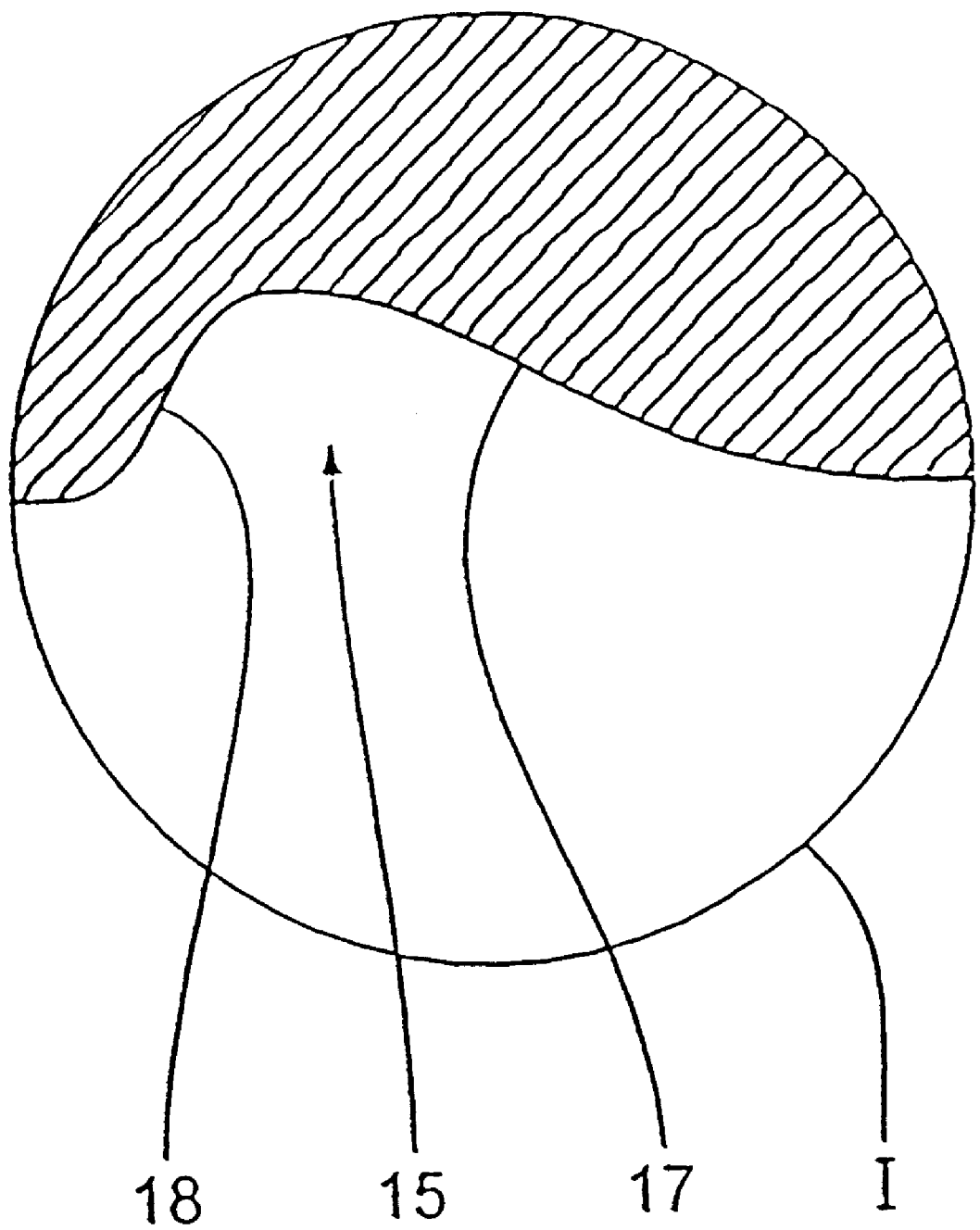
FIG. 3 shows the indentation in the shaft element of FIG. 2 in a detailed cross sectional view.

The shape of the indentation 15 is shown in detail in FIG. 3, which is a view of section I of FIG. 2. This Figure shows that the indentation 15 is nonsymmetrical and increases in depth towards the end of the pin. The indentation 15 thus has two flanks 17, 18 of different steepness, the flank 18 which faces the end of the pin being relatively steep and having only a short longitudinal dimension, whereas the flank 17 remote from the end of the pin is relatively flat but elongated and terminates in the wall of the pin.

The invention is not restricted in practice to the preferred embodiments given by way of example hereinbefore. Rather, numerous alternatives are possible which make use of the solution described while differing fundamentally in their realisation.

What is claimed is:

1. A modular endoprosthesis, comprising:
   a first shaft element having a first end, a second end, a longitudinal axis, an outer wall, a circumferential indentation and a substantially conical bore, wherein the bore includes an open mouth and a closed base; and the circumferential indentation is shaped and located on the outer wall close to the open mouth of the conical bore whereby the mechanical stress is reduced in the vicinity of the mouth of the bore by substantially evening out the mechanical stress in the direction of the longitudinal axis of the bore when the endoprosthesis is subjected to a bending force; and
   a second shaft element having a first end, a second end, a longitudinal axis, an outer wall and a substantially conical pin adapted to fit the bore in the first shaft element, for joining the two shaft elements together with a conical socket connection.

2. The modular endoprosthesis according to claim 1, wherein the circumferential indentation has a depth dimension perpendicular to the longitudinal axis of the bore and the depth of the indentation increases at least in part along the longitudinal axis of the bore in the direction of the bore mouth.

3. The modular endoprosthesis according to claim 1, wherein shear stresses are evened out.

4. The modular endoprosthesis according to claim 1, wherein, when viewed in cross section, the indentation is shaped so that it increases less sharply in depth going towards the bore mouth than it subsequently decreases again.

5. The modular endoprosthesis according to claim 1, wherein at least one shaft element is curved to resemble a natural bone.

6. The modular endoprosthesis according to claim 1, wherein the bore and pin form a press-fit.

7. The modular endoprosthesis according to claim 1, wherein at least one shaft element has a longitudinal channel for receiving a tie-rod for bracing the shaft elements.

8. The modular endoprosthesis according to claim 1, wherein one shaft element has a means for receiving an artificial ball of a joint.

9. The modular endoprosthesis according to claim 1, wherein one shaft element further includes a bone pin for anchoring the shaft element in a natural bone.

10. A modular endoprosthesis according to claim 1, comprising a femur prosthesis.

* * * * *